United States Patent
Eglin (10) Patent No.: US 7,680,086 B2
(45) Date of Patent: *Mar. 16, 2010

(54) WIRELESS LOCAL AREA NETWORK WITH CLIENTS HAVING EXTENDED FREEDOM OF MOVEMENT

(75) Inventor: Matthew George Eglin, Ottawa (CA)

(73) Assignee: Siemens Canada Limited, Ontario (CA)

( * ) Notice: Subject to any disclaimer, the term of this patent is extended or adjusted under 35 U.S.C. 154(b) by 1685 days.

This patent is subject to a terminal disclaimer.

(21) Appl. No.: 10/237,574

(22) Filed: Sep. 9, 2002

(65) Prior Publication Data

US 2004/0047320 A1 Mar. 11, 2004

(51) Int. Cl.
*H04W 4/00* (2006.01)
(52) U.S. Cl. .................. 370/338; 370/389; 370/401
(58) Field of Classification Search ............ 370/338, 370/328, 329, 331, 332, 333, 345, 349, 330, 370/389
See application file for complete search history.

(56) References Cited

U.S. PATENT DOCUMENTS

| | | | |
|---|---|---|---|
| 5,717,737 A | 2/1998 | Doviak et al. ............ 379/58 |
| 6,198,920 B1 | 3/2001 | Doviak et al. ............ 455/426 |
| 6,253,064 B1 | 6/2001 | Monroe | |
| 6,732,176 B1 * | 5/2004 | Stewart et al. ........... 709/227 |
| 6,847,620 B1 | 1/2005 | Meier | |
| 6,876,642 B1 | 4/2005 | Adams et al. | |
| 6,937,574 B1 | 8/2005 | Delaney | |
| 6,990,338 B2 * | 1/2006 | Miller et al. ............ 455/431 |
| 7,099,339 B1 * | 8/2006 | Wang et al. ............. 370/401 |
| 2002/0009078 A1 | 1/2002 | Wilson | |
| 2002/0041568 A1 | 4/2002 | Bender | |
| 2002/0061758 A1 | 5/2002 | Zarlengo et al. | |
| 2002/0087992 A1 * | 7/2002 | Bengeult et al. ........... 725/76 |

(Continued)

FOREIGN PATENT DOCUMENTS

WO WO 01/99466 A2 12/2001
WO WO 02/43348 A1 5/2002

OTHER PUBLICATIONS

White Pater: "IP Mobility vs. Session Mobility", Columbitech, 2001, http://www.columbitech.com/documents/Columbitech_IP_mobility_vs_session_mobility_WhitePaper.pdf.

(Continued)

*Primary Examiner*—Jason E Mattis
*Assistant Examiner*—Dady Chery
(74) *Attorney, Agent, or Firm*—Francis G Montgomery (57) ABSTRACT

A wireless virtual local area network (VLAN) and a device selectively connecting to the wireless VLAN over a second wireless network that may be independent of the wireless VLAN. The device is capable of connecting to at least the wireless VLAN and to the second wireless network. Wireless VLAN access points are each connected to an Ethernet aggregation switch, which is VLAN aware and matches client traffic from connected access points with access VLANs. A wireless VLAN switch maintains an association table between access VLANs and core VLANs. The second wireless network may be remotely connected over the Internet or a private network to a tunnel endpoint. The tunnel endpoint is connected to the VLAN switch, which uses the association table to manage free-form client traffic between connected devices and other mobile stations at access VLANs and appropriate core VLANs.

25 Claims, 7 Drawing Sheets

U.S. PATENT DOCUMENTS

| | | |
|---|---|---|
| 2002/0159407 A1 | 10/2002 | Carrafiello et al. |
| 2002/0191567 A1 * | 12/2002 | Famolari et al. ............ 370/335 |
| 2002/0191572 A1 | 12/2002 | Weinstein et al. |
| 2003/0142651 A1 | 7/2003 | Matta et al. |
| 2003/0198208 A1 | 10/2003 | Koos et al. |
| 2006/0190586 A1 | 8/2006 | Stewart |

OTHER PUBLICATIONS

White Pater: "Columbitech Wireless VPNTM Version 1.4", Columbitech, May 5, 2003, http://www.columbitech.com/documents/ColumbitechWVPNTechnicalDescription.pdf.

* cited by examiner

WIRELESS LOCAL AREA NETWORK WITH CLIENTS HAVING EXTENDED FREEDOM OF MOVEMENT

RELATED APPLICATION

The present application is related to U.S. patent application Ser. No. 10/140,629 entitled "LOCAL AREA NETWORK WITH WIRELESS CLIENT FREEDOM OF MOVEMENT" to Matthew G. Eglin, filed May 8, 2002, and assigned to the assignee of the present invention.

BACKGROUND OF THE INVENTION

1. Field of the Invention

The present invention is related to a wireless local area network (WLAN) and more particularly, to a WLAN with connected wireless communication devices.

2. Background Description

The Institute of Electrical and Electronics Engineers (IEEE) wireless protocol designated 802.11b is an Ethernet local area network (LAN) variant. Ethernet technology has shown an amazing ability to adapt to new requirements, evolving from a simple 10 Mbps bus to gigabit full-duplex switched networks and to wireless LANs. Ethernet is well understood and there is a wealth of experience with cost reduction and integration of Ethernet devices. Some current Ethernet interface cards (10BaseT) retail at less than $10. 802.11b wireless LAN (WLAN) card technology is subject to the same economy of scale and prices have fallen to less than 30% of their relatively recent original prices. Given its track record, Ethernet is a low-risk, extensible technology suited, for example, to address challenges in wide-area mobility.

Consequently, WLAN technology has been characterized as a disruptive technology. In other words, WLAN technology may change paradigms and lead to unexpected and unpredictable market developments. Past examples of disruptive technologies are the telephone, the personal computer (PC) and the Internet. Today, WLANs are becoming ubiquitous offering cheap solutions for both home and office networks. Currently however, there are three major limitations on WLAN technology: speed, range and security.

The 802.11b standard supports speeds of up to 11 Mbs. However, 802.11a and 802.11g are promising to deliver much higher speeds. Although range is limited, typically, to about fifty meters (50 m) outdoors, tests have demonstrated a range capability of up to 20 miles using directional antennas. Work is continuing to expand the coverage of the wireless base stations. Wired Equivalent Privacy (WEP) for wireless networks has proven far less secure than was intended. The security limitations of WEP are now well understood and work is on-going to enhance these protocols to improve the security of wireless interfaces.

The IEEE 802.1Q virtual LAN (VLAN) protocol defines interoperability operation of VLAN bridges. 802.1Q permits the definition, operation and administration of VLAN topologies within a bridged LAN infrastructure, such that LANs of all types may be connected together by Media Access Control (MAC) bridges.

Heretofore, these Ethernet LAN variants have been relatively rigidly architected. Once attached or connected, a device could communicate freely with other attached devices. If after sending a request, however, the connection is lost prior to receiving a response, the response was lost. Once reconnected, whether to the same or a different port and, even prior to arrival of the response, the response was lost and the request had to be sent anew. This is still the case for state of the art VLANs and even for devices wirelessly connected to such a VLAN. So, if a wireless device that is connected to a VLAN through an access point leaves the access point's reception area, it must re-establish communications. This is true even if it never leaves the overall LAN reception area, i.e., the area covered by all connected access points, and even if it remains in the reception area of another connected access point.

Beyond the wireless LAN coverage area, the wireless device must find some other way to connect, either wired (for example with a modem) or wirelessly. Other wireless technologies, especially wireless cell phone technologies, provide a more or less suitable connection (albeit an expensive one) when an access point isn't readily available. As wireless communications technology advances towards next generation higher speed communications, the performance of this type of alternate connection may become acceptable, but cost is still expected to be a barrier to exclusive use. So, wireless LAN connections will remain preferable.

Furthermore, manually switching between cellular (or other wireless communications technology) and a lower cost wireless LAN connection is very disruptive. Thus, someone that expects to be moving between areas where a wireless LAN connection may or may not be available, must either accept connection disruptions or pay a premium to connect to another wireless service to maintain a constant connection.

Thus, there is a need for a wireless LAN wherein a wirelessly connected device can roam freely and still maintain a connection to the wireless network, and that can maintain a connection even outside the range of the Wireless LAN using a second network

SUMMARY OF THE INVENTION

It is a purpose of the invention to improve user mobility on wireless networks;

It is yet another purpose of the invention to expand wireless device network connectivity availability;

It is yet another purpose of the invention to freely allow network clients wirelessly connected to a network to roam beyond the range of a currently connected access point while maintaining a network connection over a second network.

The present invention relates to a wireless virtual local area network (VLAN) and a device selectively connecting to the wireless VLAN either directly or indirectly over a second wireless network that may be independent of the wireless VLAN. The device includes at least two wireless network connection capabilities, one for connecting to the VLAN and the second for connecting to the second wireless network The wireless VLAN may include multiple wireless access points, each connected to an Ethernet aggregation switch. Each Ethernet aggregation switch is VLAN aware and matches client traffic from connected access points with access VLANs. A wireless VLAN switch maintains an association table between access VLANs and core VLANs. The second wireless network may be remotely connected over the Internet or a private network to a tunnel endpoint. The tunnel endpoint is connected to the VLAN switch, which uses the association table to manage free-form client traffic between connected devices and other mobile stations at access VLANs and appropriate core VLANs.

BRIEF DESCRIPTION OF THE DRAWINGS

The foregoing and other objects, aspects and advantages will be better understood from the following detailed description of a preferred embodiment of the invention with reference to the drawings, in which.

DESCRIPTION OF PREFERRED EMBODIMENTS

Figure 1:
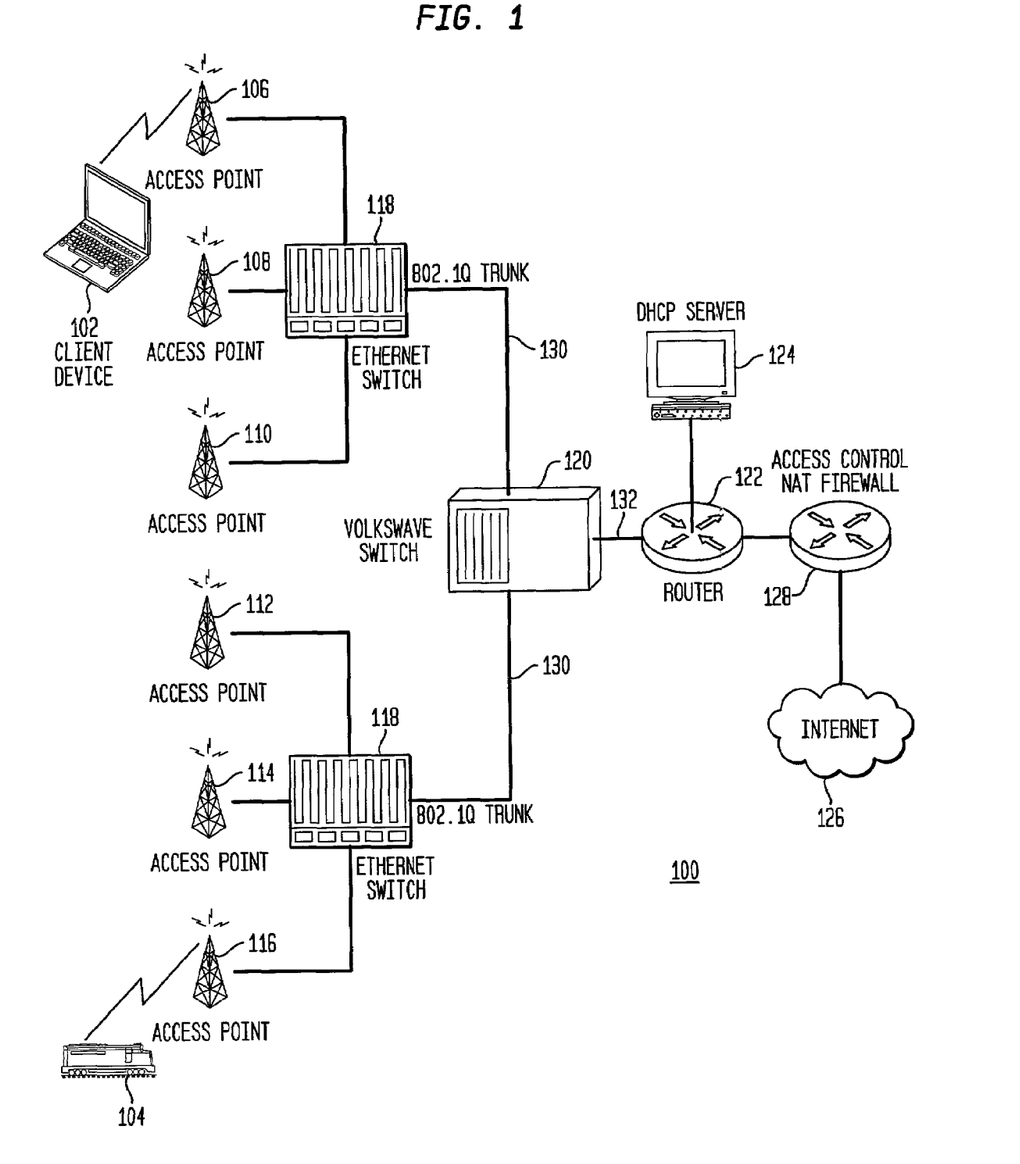
FIG. 1 shows an example of a free-form virtual local area network (FLAN)

FIG. 1 shows an example of a free-form virtual local area network (FLAN) 100 with wireless access capability as described in U.S. patent application Ser. No. 10/140,629 entitled "LOCAL AREA NETWORK WITH WIRELESS CLIENT FREEDOM OF MOVEMENT" to Matthew G. Eglin, filed May 8, 2002, and assigned to the assignee of the present invention. Wireless clients/mobile stations connect to the FLAN 100 and, once connected, roam freely within the wireless coverage area, seamlessly swapping wireless connection from one access point to another access point as they roam. The present invention extends the wireless client roaming capability beyond the FLAN wireless coverage area for appropriately equipped wireless client devices.

Normally, wireless client devices or mobile stations (MS) 102, 104 are connected by wireless data links to one of numerous access points (APs) 106, 108, 110, 112, 114, 116. Examples of such mobile stations 102, 104 or wireless client devices may include what is known as a personal digital assistant (PDA), a cellular (cell) phone (in particular an Internet capable cell phone), a notebook computer/wireless tablet, a desktop computer or, a vehicle such as a train with an on-board network that has wireless communications capability. Provided the MS 102, 104 is within range of at least one of the APs 106, 108, 110, 112, 114 or 116, connection to the FLAN 100 is through that AP 106, 108, 110, 112, 114, 116. Each AP 106, 108, 110, 112, 114, 116 is connected to an Ethernet aggregation switch 118. Each aggregation switch 118 aggregates all client traffic from connected APs 106, 108, 110, 112, 114, 116, passing it upstream to a preferred free-form virtual network switch or FLAN switch 120. Optionally, a preferred embodiment network may include more than one layer of aggregation switches 118 and/or FLAN switches 120.

Although not indicated in this example, according to a preferred embodiment of the invention in addition to WLAN connection capability, at least one MS (e.g., a PDA, cell phone, notebook computer or wireless tablet) includes at least one other wireless communications capability (e.g., cell phone capable) for connecting to another wireless network. Thus, whenever the MS strays beyond the wireless coverage area MS or otherwise loses a WLAN connection, this other, second wireless capability continues a virtual connection to the FLAN 100 through that other wireless network, thereby avoiding a service disruption. Examples of such other wireless communications capability may include a communications capability based in, Global System for Mobile Communication (GSM), General Packet Radio Service (GPRS), third generation (3G) wireless technology, code division multiple access 2000 (CDMA2000) technology or in any other appropriate wireless communications technology. For example, such a MS 102, 104 might include a CDMA2000 transceiver and an 802.11b Ethernet adapter.

The FLAN switch 120 may be connected through a typical router 122 to a typical Dynamic Host Configuration Protocol (DHCP) Server 124 and to a public network, e.g., to the Internet 126. For optional security, the router 122 also connects externally through a typical gateway 128 providing access control, network address translation (NAT) and a firewall. Each FLAN switch 120 may have multiple VLAN trunk interfaces 130, 132. FLAN switch interfaces 130 connected to aggregation switches 118 are referred to herein as access ports and packets arriving at access ports 130 are downstream packets. FLAN switch interfaces 132 connected to routers 122 are referred to herein as core ports and packets arriving at core ports 132 are upstream packets.

A VLAN-aware switch refers to an Ethernet switch that associates each frame with a single VLAN, e.g., Ethernet aggregation switch 118. A typical VLAN-aware switch includes an association table where each row contains a MAC address, a VLAN ID and a port. Thus, a VLAN aware switch forwards each frame to a MAC address based upon that single associated VLAN. By contrast, a preferred FLAN switch 120 associates each frame with two VLANs, one at an access port 130 and the other at a core port 132. To that end, each FLAN switch 120 maintains a port association table where each row contains a MAC address, an access port/VLAN pair, and a core port/VLAN pair. Further, aggregation switches 118 are configured to statically map each of the access ports to a different VLAN on its trunk port. Optionally, each aggregation switch 118 may share VLANs among multiple APs 106, 108, 110, 112, 114, 116, each one connected to a different port. VLAN sharing may be appropriate to minimize the number of VLAN IDs used. However, since there are more available VLAN IDs (4094) than ports on any one aggregation switch 118, normally, the FLAN switch 120 can reuse VLAN IDs on different aggregation switches 118 making sharing VLAN IDs unnecessary.

For FLAN 100 the transmission/reception range of each AP 106, 108, 110, 112, 114, 116 is selected such that the coverage area for each overlaps other adjacent access points providing uninterrupted service for the intended coverage area. Connected mobile stations 102, 104 can pass between access point reception areas and still remain connected in constant communication with FLAN 100, provided they remain in contact with at least one AP 106, 108, 110, 112, 114, 116. The aggregation switch 118 passes data between APs 106, 108, 110, 112, 114, 116 and FLAN switch 120, which seamlessly routes data between mobile stations 102, 104, and, for example, a selected Internet 126 address. When a mobile station 102, 104 moves from one access point reception area (e.g., 110) to another (e.g., 116), data transmission to/from the particular mobile station 102, 104 is automatically conveyed correctly over the rest of FLAN 100 without any manual intervention. Thus, the MS 102, 104 can remain connected until it leaves/is removed from the coverage area, i.e., cannot contact any of the APs 106, 108, 110, 112, 114 or 116. A mobile station equipped with a capability of connecting to at least one other wireless network according to the present invention can maintain this connection, even when it is not in the FLAN 100 coverage area.

Figure 2A:
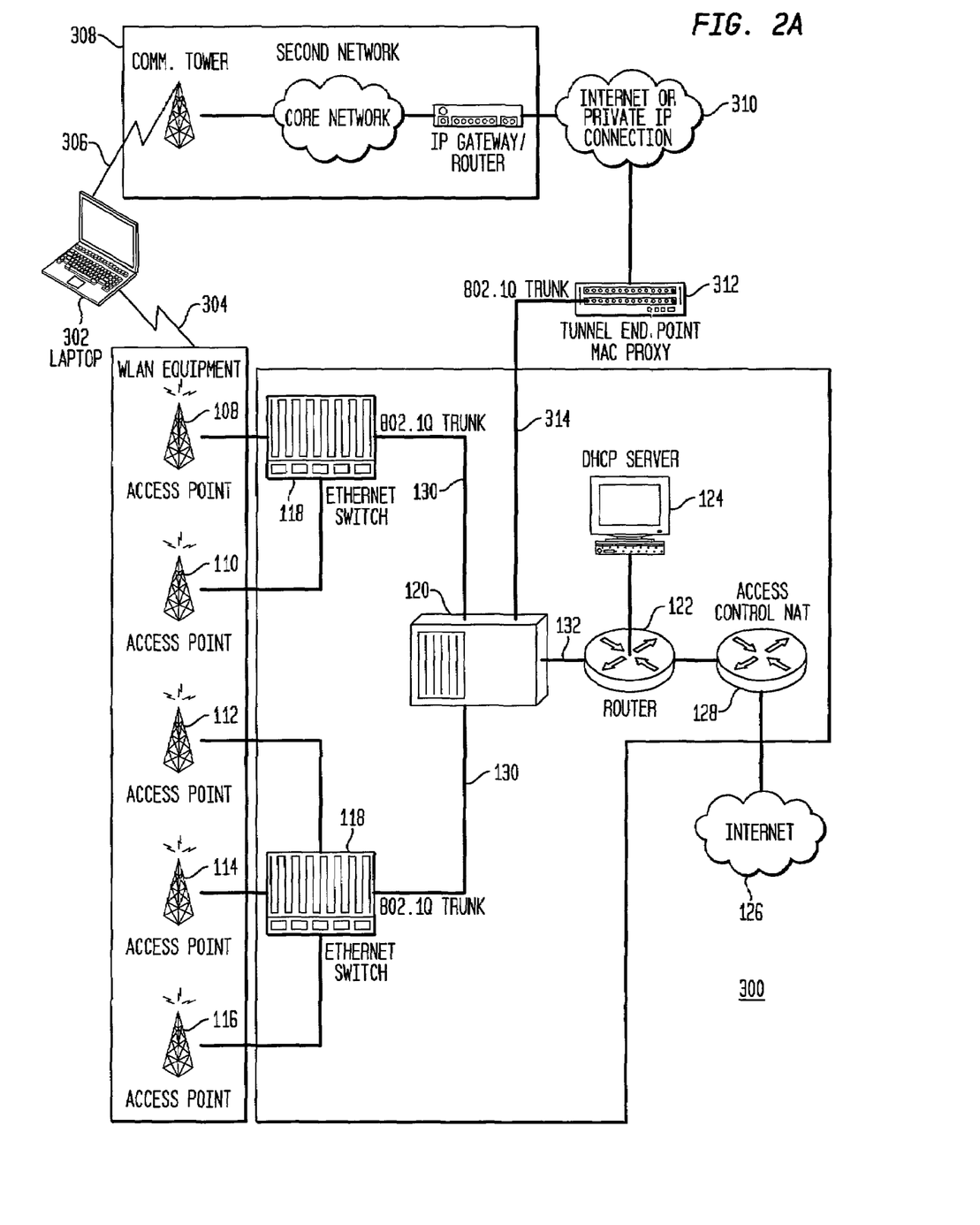
FIG. 2A shows an example of a preferred embodiment extended FLAN and mobile station (MS) capable of maintaining a connection beyond the coverage area described by the individual AP coverage areas.

So, FIG. 2A shows an example of a preferred embodiment extended FLAN 300 according to the present invention with elements identical to those of FLAN 100 in FIG. 1 labeled identically. The connection region for MS 302 extends beyond the coverage area described by the individual AP coverage areas. Each MS 302 has at least two independent wireless communication capabilities, preferably a WLAN capability 304 (e.g., through an on-board WLAN card or interface) for communicating both to APs 108, 110, 112, 114 and 116 and an alternate communications protocol connection 306 (e.g., through a cell phone module) to alternate connection wireless network 308. This second or alternate connection second wireless network 308, which may itself be another WLAN interface, connects over the Internet or over a private network 310 to an appropriate tunnel endpoint 312, which provides an Ethernet Bridge across the particular second wireless network 308. Tunnel endpoint 312 is connected to FLAN switch 120 over an VLAN trunk interface 314, which is substantially identical to access ports 130.

In this example MS 302 includes both a WLAN connection capability (e.g., 802.11b wireless Ethernet) and at least one alternate or second wireless communications capability, e.g., CDMA2000, GSM, GPRS or 3G. It should be noted that while wireless client devices such as MS 102, 104 of FIG. 1 with a single wireless capability connecting to APs 108, 110, 112, 114 and 116, but without the capability to connect to a second network may be included in an extended FLAN 300 of the present invention; they would not normally have access to the FLAN 300 outside of the coverage area afforded by APs 108, 110, 112, 114, 116. Further, whenever it is in range, MS 302 communicates with the FLAN 300 through an AP 108, 110, 112, 114 or 116 identically with MS 102, 104.

Figure 2B:
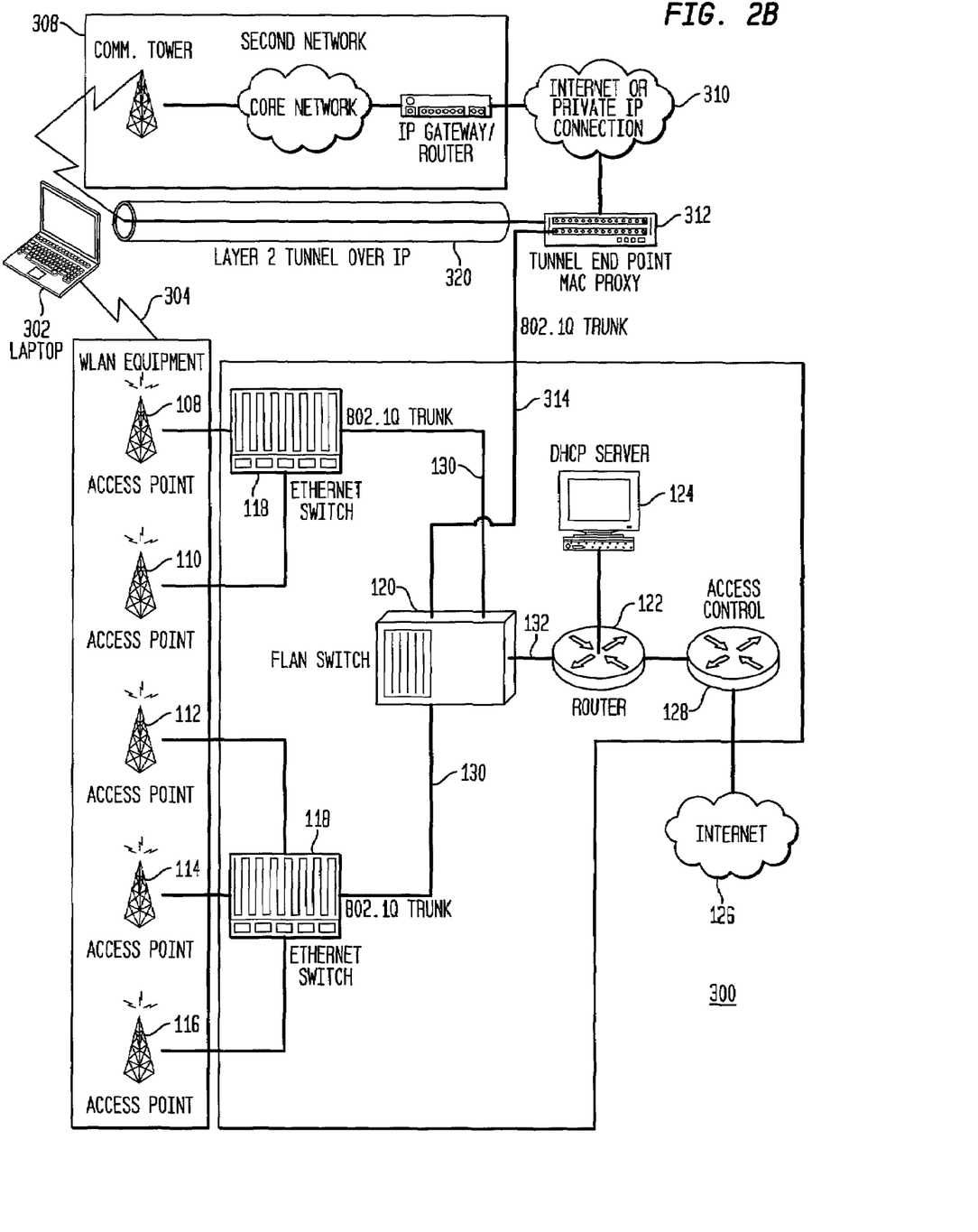
FIG. 2B shows the MS tunneling through a second wireless network to maintain the connection with the FLAN.

As shown in FIG. 2B, whenever the client (MS 302) strays beyond the AP coverage area or for whatever reason cannot connect to an AP 108, 110, 112, 114 or 116, e.g., when access point carrier signal fails below a selected level indicating the absence of an available AP108, 110, 112, 114, 116, MS 302 automatically switches to its alternate connection through second network 308. Monitoring signal strength is well known and displayed on most commercially available cell phones. When MS 302 switches connection, it sends packets through a layer 2 tunnel 320 that to the FLAN 300 appears to be the client's WLAN interface. Ethernet frames or packets containing the MAC and IP addresses of the client's WLAN interface (e.g., WLAN card) tunnel over the second network to the tunnel endpoint 312. The tunnel endpoint 312 terminates the layer 2 tunnel 320 and passes Ethernet frames from clients (e.g., MS 302) over VLAN trunk interface 314 to FLAN switch 120. Each such connected MS 302 maintains this layer 2 tunnel 320, which carries Ethernet packets across the second network 308 to the tunnel endpoint 312 and then, to the FLAN switch 120, thereby seamlessly maintaining connection to the FLAN 300.

When the connection switches to the second network 308, FLAN switch 120 just sees another port change for the client, a normal FLAN mobility event. Thus, the switch to the second network 308 is invisible to the FLAN 300. When the client moves back into the connection area, it (MS 302) may automatically terminate the layer 2 tunnel 320 and switch its connection from the second network interface, i.e., from 306 to 304 in FIG. 2A. This switch is simply made by resuming Ethernet Frame transmission on the WLAN interface 304, again a normal FLAN mobility event. The layer 2 tunnel may be maintained, but not used, while the client is connected to the WLAN, if the network requires very fast hand-off from WLAN to the second network.

Figure 3A:
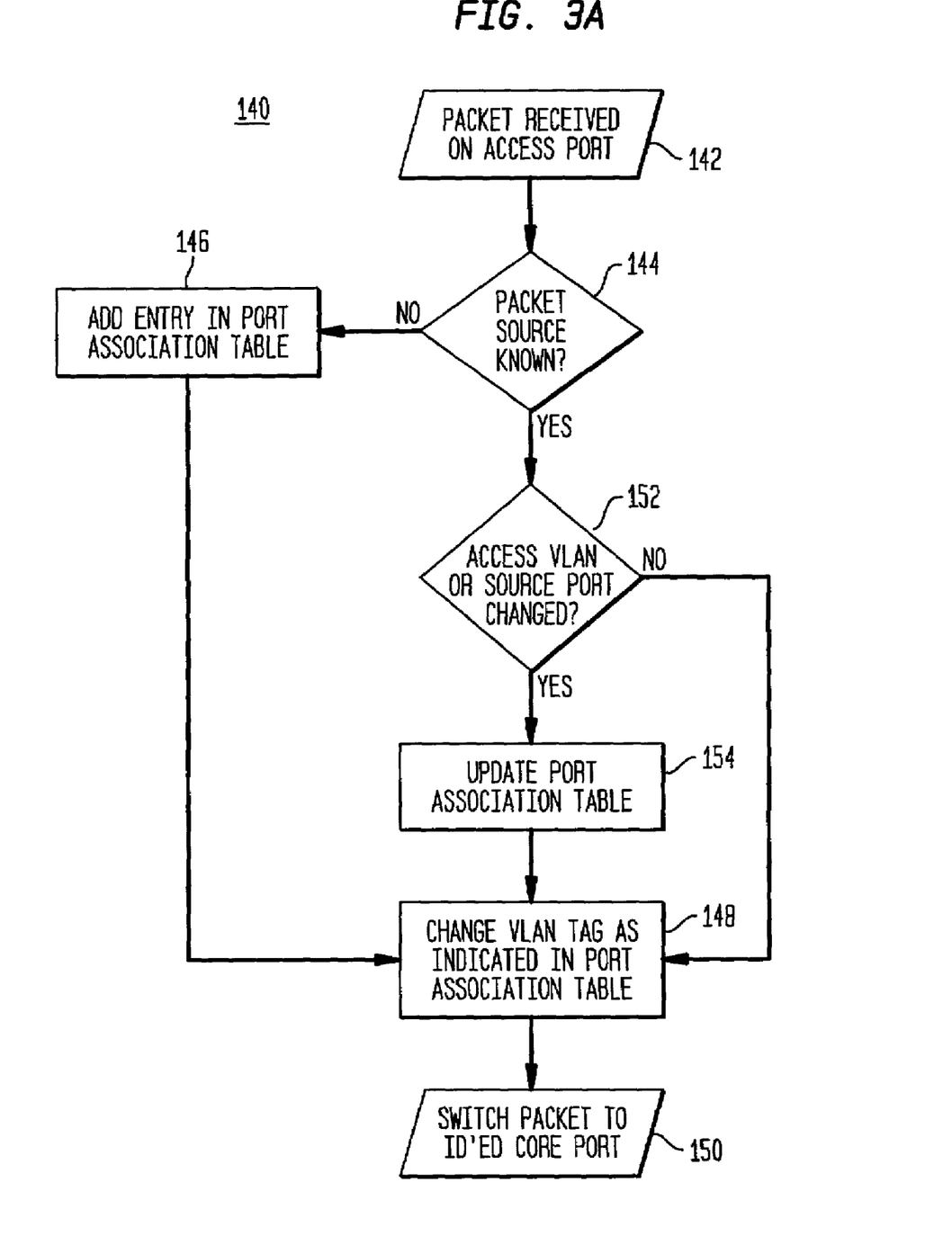
FIGS. 3A-B show flow diagrams for FLAN switch packet handling, downstream packets at access ports and upstream packets at core ports.
Figure 3B:
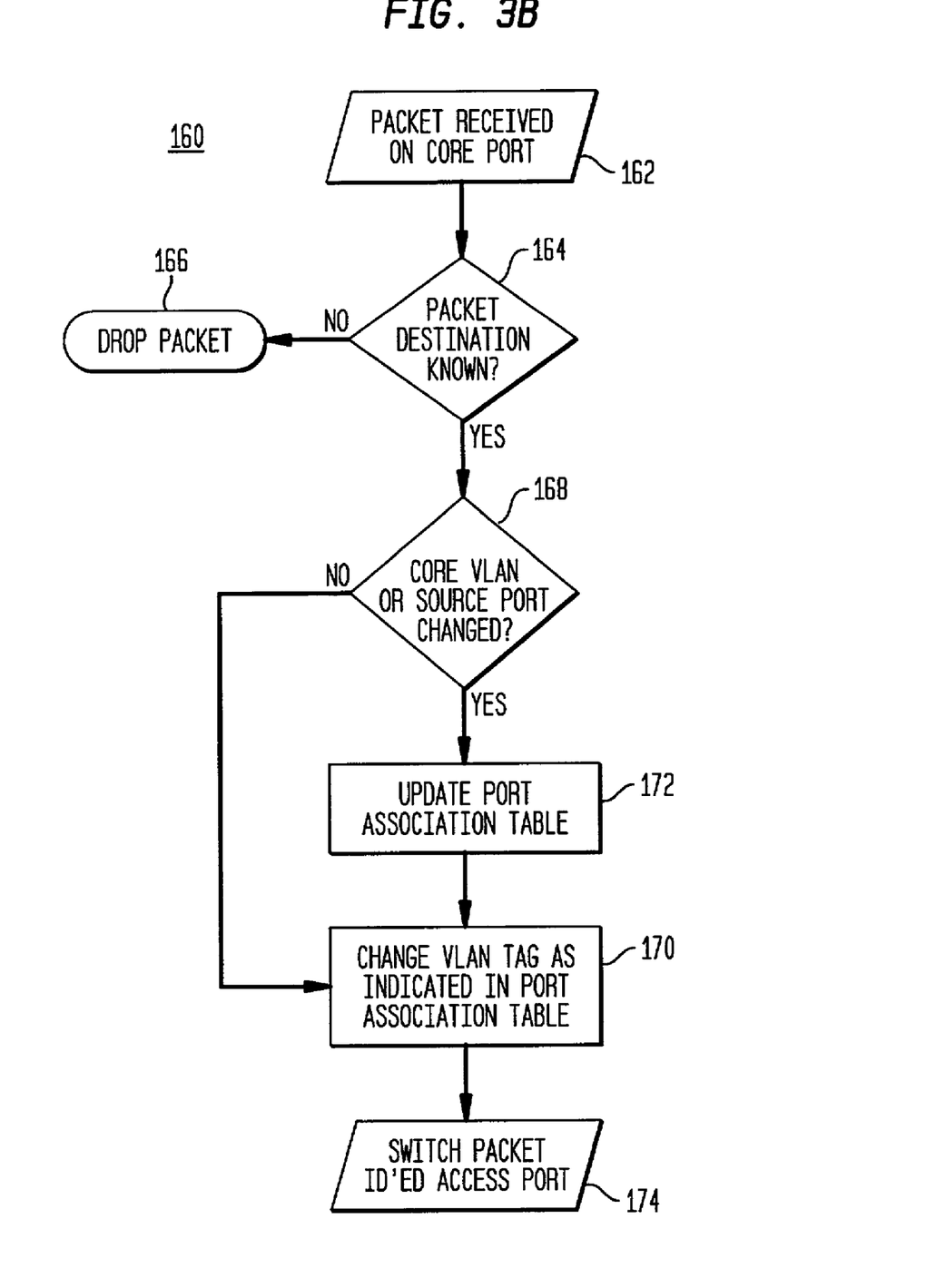

FIGS. 3A-B show flow diagrams for FLAN switch packet handling for downstream packets at access ports in flow diagram 140 and, for upstream packets at core ports in flow diagram 160 according to a preferred embodiment of the present invention. In FIG. 3A a downstream packet is received at an access port in step 142. If the downstream packet is a DHCP request, the router (122 in FIGS. 1 and 2A-B) acts as a DHCP relay agent and passes the packet to the DHCP Server 124. The DHCP Server 124, in addition to otherwise functioning as a normal DHCP Server, returns an address to the client, thereby configuring the client (e.g., MS 102, 104 and 302) and, switches to pass the traffic. The DHCP Server 124 can re-assign the client 102, 104, 302 to a subnet that does not match a default VLAN assigned by the FLAN switch 120. When the MS 102, 104, 302 is assigned to a subnet other than the default, the DHCP response is directed to the appropriate DHCP relay agent and on to the correct VLAN.

So, continuing in step 144 the port association table is checked to determine if the frame includes the MAC address of a currently connected MS 102, 104, 302. If the packet does not originate from a current connection, then in step 146, a new connection is configured by entering the source MAC address, the access port/VLAN and default core port/VLAN information in the port association table. The default core port/VLAN is related to the incoming access port/VLAN. In step 148 the appropriate VLAN tag is changed to reflect the new default core VLAN for the downstream packet. Then, in step 150 the packet is switched to the default core port. If in step 144, however, the MAC address is identified as being to a currently connected MS 102, 104, 302, then in step 152, the port association table is checked to determine if the access port/VLAN has changed. The access port/VLAN may change when the mobile station (e.g., 302) roams between AP reception areas or in and out of the coverage area, e.g., out of the coverage area at first wireless access point 110 in FIG. 1 and, later, back into the coverage area at another wireless access point 116. If the access port/VLAN is unchanged, then, continuing to step 148 the package is updated with the appropriate VLAN tag and in step 150 switched to the appropriate identified core port. Otherwise, if the access port/VLAN is changed in step 152; then, in step 154 the port association table is updated and in step 148 the VLAN tag is changed. Then, in step 150 the packet is switched to the appropriate identified core port.

Similarly, in step 162 of FIG. 3B, when a packet is received at a core port, in step 164 the packet frame is checked for a known destination. If the upstream packet is not directed to a known destination, then, it is not intended for any currently connected MS (e.g., 102, 104 or 302) and, in step 166 the packet is dropped. If, however, the frame includes the destination MAC for a connected MS 102, 102 or 302, the packet is for a known destination. Then, in step 168, the association table is checked to determine if the client association has changed from the most recent communication with that client. The association table may have changed because the identified core VLAN may have changed in a DHCP response or, because the MS 102, 104, 302 has been assigned to a VLAN other than the default for its incoming port. Also, the VLAN and the port may both change if there is a fail over to a backup router. If the client association is unchanged, then, in step 170 the VLAN tag is changed to reflect the correct access VLAN for the packet. If the port association has changed, then in step 172 the port association table is updated before the VLAN tag is changed in step 170. Then, in step 174 the packet is switched to its access port.

So, for a packet traveling from a mobile station 102, 104 on layer 2 of the access network on the access side of the FLAN switch 120 or from MS 302 over the second communications network; the packet is assigned to a VLAN based on the mobile station's physical location in the network, i.e., the port for its connected Access Point 106, 108, 110, 112, 114, 116 or from tunnel endpoint 312. A packet on the core side of the FLAN switch 120 traveling to a mobile station, is assigned to a VLAN based on the mobile station's logical location in the network, or, equivalently, the mobile station's IP subnet.

Figure 4:
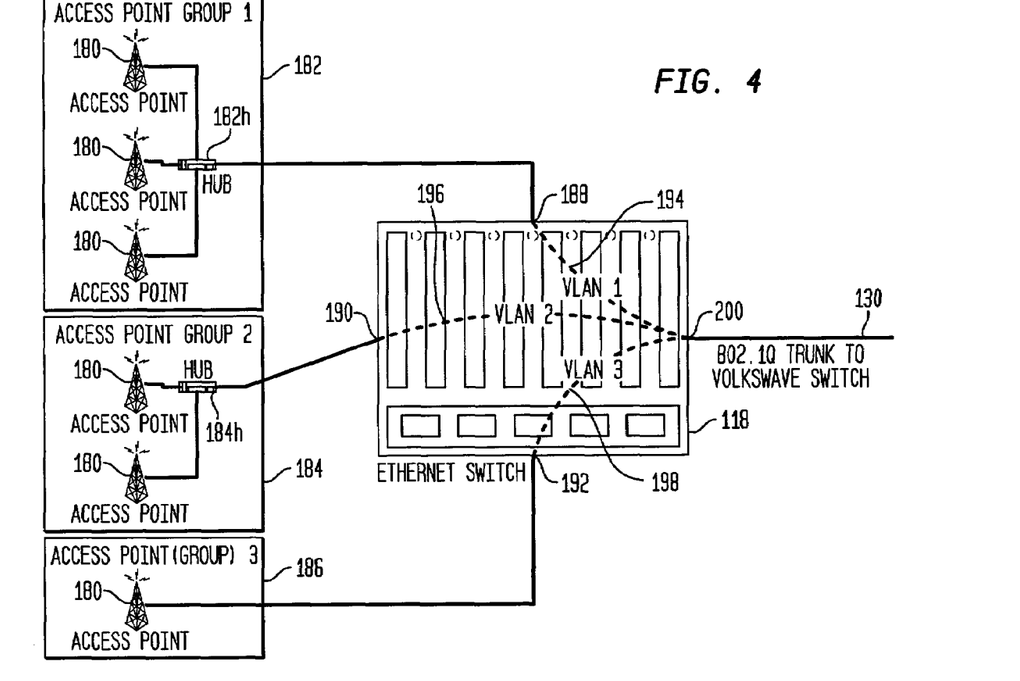
FIG. 4 is an example of VLAN configuration of an Ethernet aggregation switch.

FIG. 4 is an example of VLAN configuration of an Ethernet aggregation switch 118 according to a preferred embodiment of the present invention. Preferably, the FLAN switch 120 meshes through VLAN trunk interface 130 with the VLAN configuration of Ethernet aggregation switches 118, the router 122 and the tunnel endpoint 312. In this example, APs 180 are grouped and each group 182, 184, 186 is connected through a hub 182h, 184h, if appropriate. Hubs 182h, 184h and individual APs (i.e. single AP groups 186) are connected to Ethernet aggregation switch ports 188, 190, 192. Each of these Ethernet switch ports 188, 190, 192 is mapped to an individual VLAN 194, 196, 198 on a VLAN trunk 200 connected to a FLAN access port. Each AP group 182, 184, 186 is mapped individually; there are no layer 2 connections between the AP groups 182, 184, 186 within the Ethernet aggregation switch 118.

Figure 5:
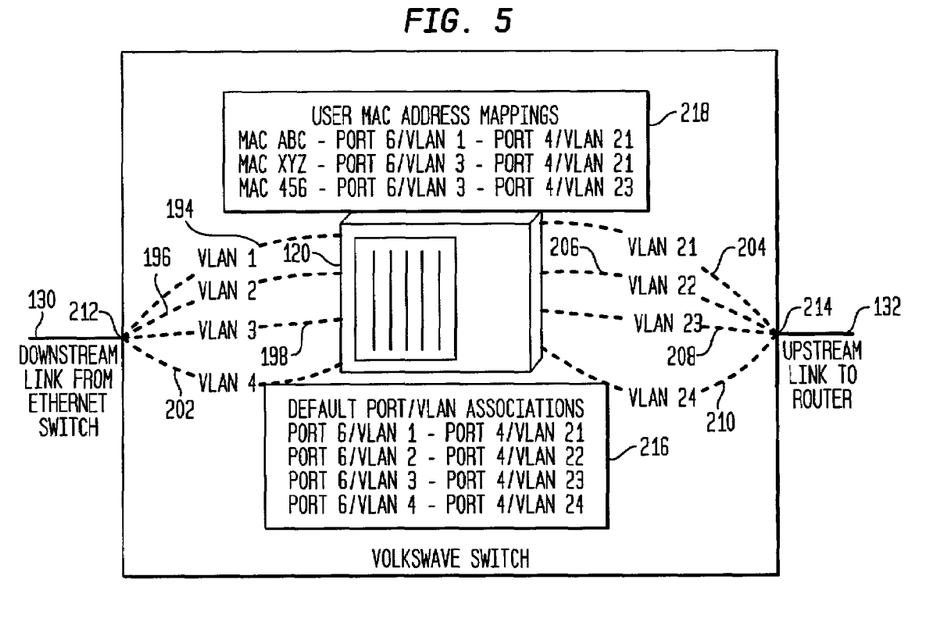
FIG. 5 shows an example of how a preferred FLAN switch preprogrammed with default relationships relates VLAN/ports.

FIG. 5 shows an example of how a preferred FLAN switch 120, preprogrammed with default relationships, relates VLANs 194, 196, 198, 202, 204, 206, 208, 210 on access port 212 and core port 214 of the FLAN switch 120. Default association table 216 provides default VLAN pairs as well as fixed core VLAN assignment for the FLAN switch 120. Devices that access special networks or devices requiring fixed IP addresses are assigned by MAC address in association table 218. These relationships may be stored in clear text configuration files and modified using any suitable text editor.

In this example, the FLAN switch 120 is aware of three mobile stations with MAC addresses ABC, XYZ and 456, all at Port 6, as indicated in association table 218. The VLAN ID numbers (e.g., 1, 2, 3, 4, 21, 22, 23, 24) are unique, but a port/VLAN tuple identifies the source and destination of a packet. Thus, VLAN ID numbers are freely reusable for all interfaces. In this example, devices ABC and 456 are in their default VLAN associations as indicated in default association table 216. By contrast, device XYZ is not in the default VLAN association for port 6. Instead, its association connects it to VLAN 204. So, for this example, device XYZ may have been moved from the second wireless network back into range of an Access Point.

Figure 6:
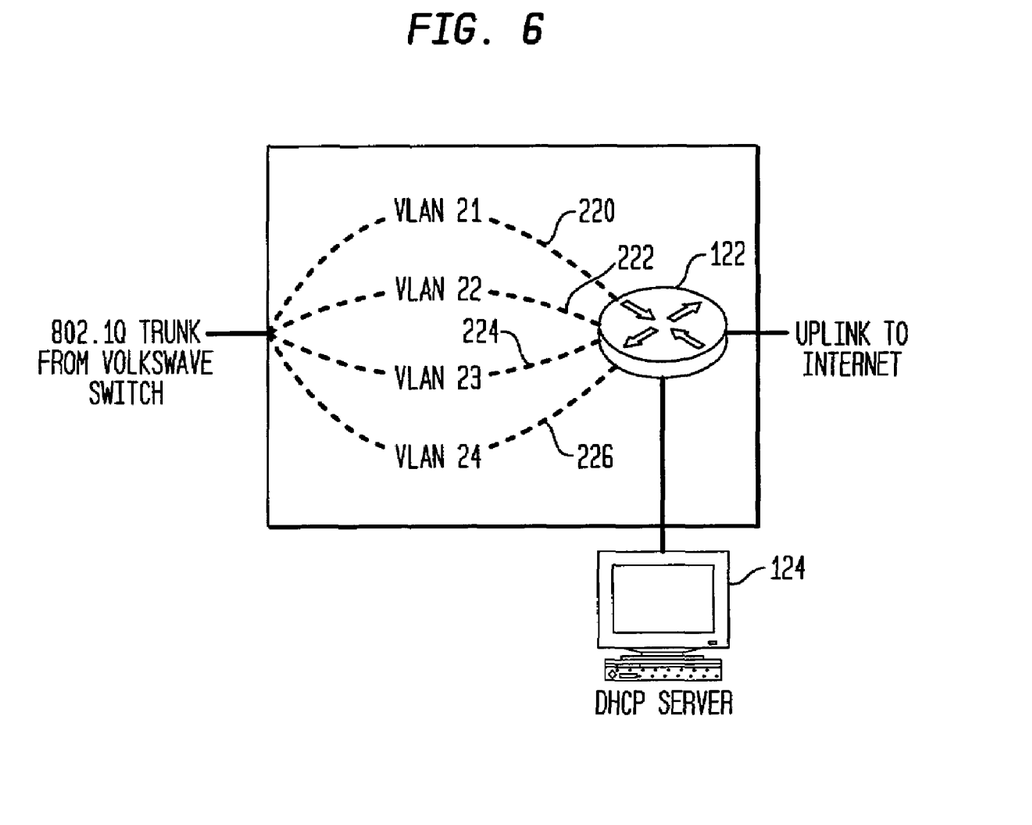
FIG. 6 shows an example of how the core VLANs are mapped to logical interfaces.

FIG. 6 shows an example of mapping the core VLANs (e.g., 204, 206, 208, 210 of FIG. 5) to logical interfaces 220, 222, 224, 226 on the router 122. In this example, each logical interface 220, 222, 224 226 is configured to provide DHCP relay; the DHCP server 124 uses the relay agent IP address (i.e., the giaddr field in the DHCP message body) to determine the appropriate IP subnet. Different sub-interfaces within the router 122, each corresponding to a different incoming VLAN, 220, 222, 224, 226 may be configured with different rules, e.g., for Internet access. For example, administrative users may be assigned to a separate administrative VLAN with access to servers that are not available to general users. The DHCP server may be modified to respond on a different VLAN, enabling the DHCP server to control VLAN assignment on the core side of the FLAN switch.

So, for example, by including a tunnel endpoint between the Internet and a corporate FLAN, appropriately equipped wireless client devices can maintain a connection to the corporate FLAN, on campus and off. A notebook computer with both an 802.11b interface and a GPRS interface can connect on-campus to the corporate 802.11b network and continue the connection through its GPRS device as it is taken off-campus. Conversely, the notebook computer can join the network off campus through its GPRS device and on-campus switch seamlessly to the 802.11b connection from the public network.

Similarly, a corporate Internet protocol (IP) based private branch exchange (PBX) may be extended for wireless stations by application of the present invention, e.g., for a wireless phone with both WLAN and 3G, GPRS or CDMA capability. A call may be initiated within the PBX network on such a wireless phone and continued outside of the WLAN receiving area over the second network. Even outside of the WLAN receiving area, an apparent PBX call can be initiated over the second network and, as the caller returns to the WLAN receiving area, the call is continued and completed over the WLAN as an in network PBX call. In particular, using what is known as Wireless Mobility for Next Gen Networks (NGN) and more particularly a NGN voice over IP (VoIP) network, the NGN core includes a tunnel endpoint. Thus, such an NGN core is capable of supporting connections from MSs from the second network.

Likewise, by providing a VoIP gateway and Internet connection in a single appliance, for example, the advantages of the present invention may be realized almost anywhere, e.g., in a private home. In particular, a home user can use a single, appropriately equipped cell phone both in-home and out, connecting cheaply over the Internet, when possible, and otherwise using precious cell phone minutes only as needed.

Advantageously, the present invention expands the reach of large free-form wireless data networks, i.e., FLANs that permit end-user mobility such as described in U.S. patent application Ser. No. 10/140,629 entitled "LOCAL AREA NETWORK WITH WIRELESS CLIENT FREEDOM OF MOVEMENT" to Matthew G. Eglin, filed May 8, 2002, and assigned to the assignee of the present invention. By inclusion of a state of the art tunnel endpoint with the Eglin FLAN, clients can connect to FLANs established, e.g., in airports, coffee shops, dense urban areas, and aboard trains and buses; and without losing that connection leave and return to the original connection location. Further, the present invention extends free-form wireless access using industry-standard wireless communications technology, e.g., GSM, GPRS, 3G, 802.11b and 802.11a. Combining available wireless access technologies, e.g., a laptop computer with cell phone capability or wireless modem and an 802.11b card, enables clients to connect to the FLAN using Internet Protocol (IP) without regard to location, whether at the office, at home or traveling across country by rail. Thus, the present invention extends the FLAN, which provides a simple and easy to manage network where existing client devices can "turn on and go" moving freely, beyond FLAN AP reception areas. Further, if desired, authorization and accounting (AAA) as well as other wireless security features may be included just as with any other state of the art network.

The present invention provides all of these advantages with a layer-two Ethernet network to interconnect the wireless access points and an alternate network. The usual scalability problems of such a network are avoided through a preferred application of IEEE 802.1Q Virtual LANs (VLANs) to effectively partition the network into many smaller networks, thus avoiding problems with broadcast traffic and spanning trees.

While the invention has been described in terms of preferred embodiments, those skilled in the art will recognize that the invention can be practiced with modification within the spirit and scope of the appended claims.

What is claimed is:

1. A network with wireless access capability comprising:
   a plurality of wireless access points with a first communications protocol;
   at least one Ethernet aggregation switch, ones of said plurality of access points being connected to each said at least one Ethernet aggregation switch, each said Ethernet aggregation switch being virtual LAN (VLAN) aware and matching client traffic from connected said access points with access VLANs;
   a free-form virtual network switch with a plurality of VLAN trunk interface ports, each said at least one Ethernet aggregation switch connected to one of said plurality of VLAN trunk interface ports, client traffic passing between said access VLANs at each said connected Ethernet aggregation switch and appropriate core VLANs; and
   at least one tunnel endpoint connecting to an access VLAN at one of said plurality of VLAN trunk interface ports and bridging an other wireless network through a tunnel to said free-form virtual network switch, said other wireless network having a second communications protocol different than said first communications protocol, wherein client wireless devices having contact with said other wireless network selectively connect to said free-form virtual network switch through said tunnel endpoint wherever said plurality of wireless access points are unavailable.

2. A network as in claim 1, the free-form virtual network switch maintaining an association table between said access VLANs and said core VLANs at said plurality of VLAN trunk interface ports.

3. A network as in claim 1, wherein said at least one tunnel endpoint is an endpoint to an Internet Protocol (IP) tunnel through another network and both the other wireless network and said at least on tunnel endpoint are connect to said other network, traffic between said other wireless network and said at least one tunnel endpoint passing through said other network, and at least one mobile station having at least two independent wireless communication capabilities for said first communication protocol and said second communication protocol, wherein said at least one mobile station is wirelessly connectable to said plurality of access point as a client wireless device and connectable to said other wireless network, said at least one mobile station communicating with said network through an available one of said plurality of access points and automatically switching connection to said other wireless network when none of said plurality of access point are available.

4. A network as in claim 3 wherein said other network includes the Internet and when connection to said at least one mobile station is switch to said other wireless network, said at least one mobile station tunnel IP packet identified for said mobile station across said other wireless network to said least one tunnel endpoint.

5. A network as in claim 3 wherein when connection to said at least one said at least one mobile station is switched to said other wireless network, said at least one mobile station maintains an IP layer 2 tunnel carrying Ethernet packets across said other wireless network to said at least on tunnel endpoint, said Ethernet packet containing a MAC and IP addresses of the VLAN interface in said at least on mobile station, whereby connection to the network is seamlessly maintained.

6. A network as in claim 5 wherein when said other network is a private network and when said at least one tunnel endpoint terminates said layer 2 tunnel passing Ethernet frames from said client wireless devices over said one VLAN trunk interface port to said free-form virtual network switch and is a proxy for said MAC address.

7. A network as in claim 1 wherein as said client wireless devices move between reception areas and switches connection between said access points and said other wireless network, said free-form virtual network switch identifies each switch and updates an association table for said each said switch.

8. A network as in claim 1 further comprising:
   a router connected to a core VLAN at another one of said plurality of VLAN trunk interface port and routing traffic on said core VLANs between said virtual network switch and a public network;
   a dynamic host configuration protocol (DHCP) server managing connection between said free-form virtual network switch and said public network; and
   a gateway providing access control, network address translation and firewall security at said public network.

9. A network as in claim 1 wherein at least two of said access points are connected to a hub forming an access point group, said hub connecting said access point group to said Ethernet aggregation switch.

10. A network as in claim 3 wherein said first communication protocol is a wireless Ethernet protocol and said second communications protocol is a cell phone network protocol.

11. A network as in claim 10 wherein said at least one mobile station comprises:
    a wireless LAN interface, wirelessly communicating with available ones of said plurality of access points; and
    a cell phone selectively communicating with said other wireless network, said at least one mobile station seamlessly maintaining connection to said network.

12. A network as in claim 11 wherein said wireless LAN interface monitors access point carrier signals and provides an indication of the presence/absence of said access point carrier signals, said client wireless devices connected to said to free-form virtual network switch through said tunnel endpoint, reconnecting to one of said plurality of access point wherever an access point carrier signals present.

13. A network as in claim 11 wherein said network is a private branch exchange network (PBX) and said wireless LAN interface is a voice over Internet protocol (VoIP) interface.

14. A network as in claim 1 wherein said other wireless network is one of a plurality of other wireless protocol bridged to said network through said tunnel endpoint.

15. A network with wireless access capability comprising:
    a plurality of wireless access points with a first communications protocol;
    a plurality of mobile stations wirelessly connectable to said plurality of access points, at least one mobile station connectable to at least one other wireless network each having a communications protocol different than said first communications protocol;
    Ethernet aggregation means for connecting ones of said plurality of access points to said network, said Ethernet aggregation means being virtual LAN (VLAN) aware and matching client traffic from said plurality of access points with access VLANs;
    free-form virtual network switching means for switching client traffic between said access VLANs at said Ethernet aggregation means to appropriate core VLANs, said free-form virtual network switching means having a plurality of VLAN trunk interface ports, each said at least one Ethernet aggregation means connected to one of said plurality of VLAN trunk interface ports; and tunnel endpoint means for terminating Ethernet packets tunneling over other wireless networks and providing terminated said Ethernet packets as client traffic to said free-form virtual network switching means, said tunnel endpoint means connected to an access VLAN at one of said plurality of VLAN trunk interface ports and bridging said free-form virtual network switching means through a tunnel to said other wireless network and providing a MAC address proxy for connected one of said at least one mobile station, said free-form virtual network switching means switching client traffic from said tunnel endpoint means to appropriate core VLANs wherever said plurality of wireless access points are unavailable.

16. A network as in claim 15, wherein said at least one mobile station comprises:
   first communications protocol means for wirelessly communicating with said network through an available one of said plurality of access points;
   second communications protocol means for wirelessly communicating with one said at least one other wireless network;
   means for automatically switching to one of said other wireless network when none of said plurality of access points are available; and
   means for automatically reconnecting to one of said plurality of access points wherever one is available, said at least one mobile station seamlessly maintaining connecting to said network.

17. A network as in claim 15, wherein said at least one tunnel endpoint is an endpoint to an Internet protocol (IP) tunnel through another network and both the other wireless network and said tunnel endpoint means are connected to said other network, traffic between said other wireless network and said tunnel endpoint means passing through said other network, and the free-form virtual network switching means comprises:
   means for maintaining an association table between said access VLANs and said core VLANs at said plurality of VLAN trunk interface ports.

18. A network as in claim 16 wherein said other network is a private network and said at least one mobile station further comprises:
   IP tunneling means for tunneling IP packet identified for said mobile station across said one of the other wireless network and said private network to said tunnel endpoint.

19. A network as in claim 15 wherein when said other network includes the Internet and said at least one mobile station comprises:
   means for maintaining an IP layer 2 tunnel carrying Ethernet packets across said other wireless network and the internet between said tunnel endpoint and said at least one mobile station, said Ethernet packets containing a MAC and IP addresses of a first communications protocol interface in said at least one mobile station, said mobile station seamlessly maintaining an FLAN connection.

20. A network as in claim 15, wherein said free form virtual network switching means comprises:
   means for identifying each switch between reception areas and switching between said access points and each of said other wireless networks; and
   means for updating an association table responsive to said each said switch.

21. A network as in claim 15 further comprising:
   traffic routing means for routing core VLAN traffic between said virtual network switch and a public network, said traffic routing means connected to a core VLAN at another one of said plurality of VLAN trunk interface ports;
   dynamic host configuration protocol (DHCP) server means for managing connection between said free form virtual network switch and said public network; and
   means for providing access control, network address translation and firewall security at said public network.

22. A network as in claim 15 further comprising:
   access point grouping means for grouping at least two of said access points into an access point group and connecting said access point group to said Ethernet aggregation means.

23. A network as in claim 16 wherein said second communications protocol means comprises cell phone communication means for communication with a cell phone network.

24. A network as in claim 23 wherein said network is a private branch exchange network.

25. A network with wireless access capability comprising:
   a plurality of wireless Ethernet access points;
   at least one Ethernet aggregation switch, one of said plurality of access points being connected to each said at least one Ethernet aggregation switch, each said Ethernet aggregation switch being virtual LAN (VLAN) aware and matching client traffic from connected said access points with access VLANs;
   a free-form virtual network switch passing client traffic between said access VLANs at each said connected Ethernet aggregation switch and appropriate core VLANs; and
   at least one IP tunnel endpoint to an IP layer 2 tunnel bridging a cell phone network to said free-form virtual network switch, wherein client wireless Ethernet devices having contact with said cell phone network seamlessly connect to said free-form virtual network switch through said cell phone network to said IP tunnel endpoint whenever said plurality of wireless Ethernet access points are unavailable.

* * * * *